United States Patent [19]

Quinn et al.

[11] Patent Number: 5,308,325
[45] Date of Patent: May 3, 1994

[54] RETENTION BALLOON FOR PERCUTANEOUS CATHETER

[75] Inventors: David G. Quinn, Grayslake; Erik Andersen, Gurnee, both of Ill.

[73] Assignee: Corpak, Inc., Wheeling, Ill.

[21] Appl. No.: 646,889

[22] Filed: Jan. 28, 1991

[51] Int. Cl.⁵ .................. A61M 29/00; A61M 5/32
[52] U.S. Cl. .................... 604/96; 604/174; 604/175; 604/264
[58] Field of Search ............... 604/96-103, 604/30, 34, 247, 246, 264, 93, 104, 167, 174, 256, 277, 278; 606/192-194; 600/29, 31; 128/768, 766

[56] References Cited

U.S. PATENT DOCUMENTS

| | | | |
|---|---|---|---|
| 3,640,282 | 2/1972 | Kamen et al. | 128/351 |
| 3,799,173 | 5/1974 | Kamen | 128/351 |
| 3,831,587 | 8/1974 | Boyd | 606/192 |
| 3,889,685 | 6/1975 | Miller, Jr. et al. | 604/97 |
| 4,148,319 | 4/1979 | Kasper et al. | 604/96 |
| 4,344,434 | 8/1982 | Robertson | 128/283 |
| 4,531,943 | 7/1985 | Van Tassel et al. | 604/96 |
| 4,574,173 | 3/1986 | Bennett | 604/96 |
| 4,779,611 | 10/1988 | Grooters et al. | 604/96 |
| 4,820,270 | 4/1989 | Hardcastle et al. | 604/96 |
| 4,822,338 | 4/1989 | Longmore et al. | 604/96 |
| 4,900,306 | 2/1990 | Quinn et al. | 604/97 |
| 4,943,275 | 7/1990 | Stricker | 604/96 |
| 4,946,440 | 8/1990 | Hall | 128/772 |
| 4,990,139 | 2/1991 | Jang | 606/192 |
| 5,059,178 | 10/1991 | Ya | 604/101 |

Primary Examiner—C. Fred Rosenbaum
Assistant Examiner—Mark Bockelman
Attorney, Agent, or Firm—Wallenstein, Wagner & Hattis, Ltd.

[57] ABSTRACT

An improved construction for an expandable and contractible retention member, such as a balloon, for body access tubes, to retain a distal open end of the tube against an inner body cavity wall of the patient. The balloon is secured to only the inner and outer peripheral edges of the distal open end of the tube by a sleeve. The sleeve has both an outer wall and an inner wall which receives, respectively, the outer and inner walls of the tube. The balloon includes an outer wall and an inner wall which defines an inflation chamber. The inflation chamber extends beyond the distal open end of the tube so that no portion of the tube passes through the chamber. The balloon includes an axial opening to permit passage of fluid out of the tube.

5 Claims, 3 Drawing Sheets

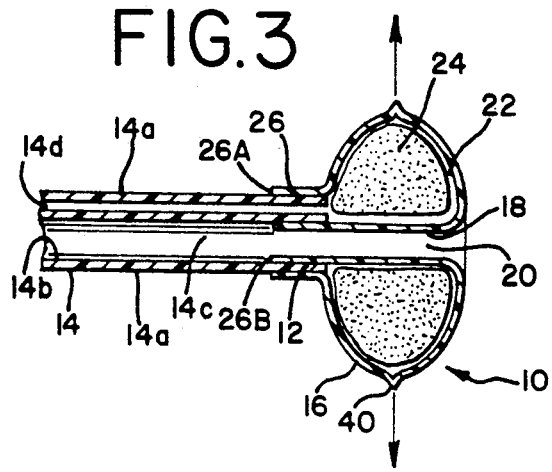
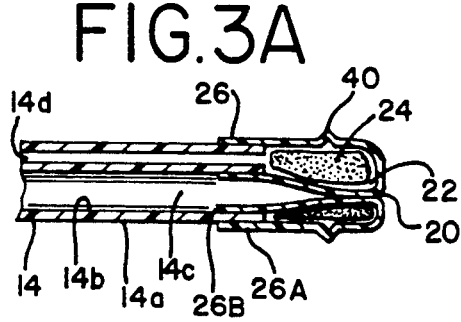
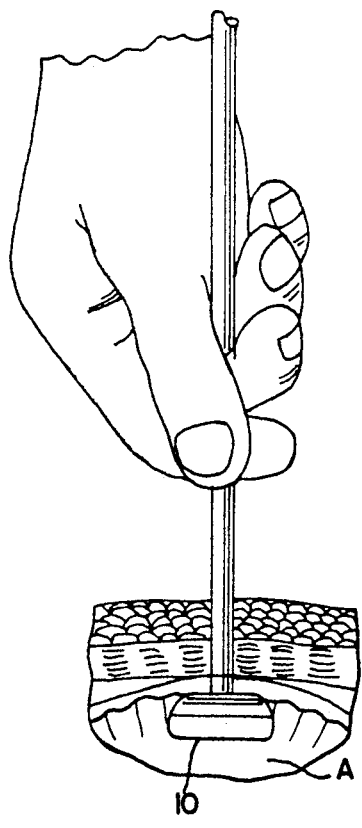
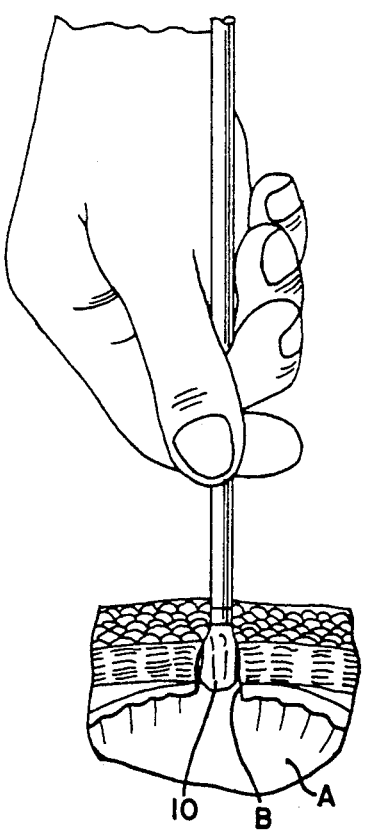
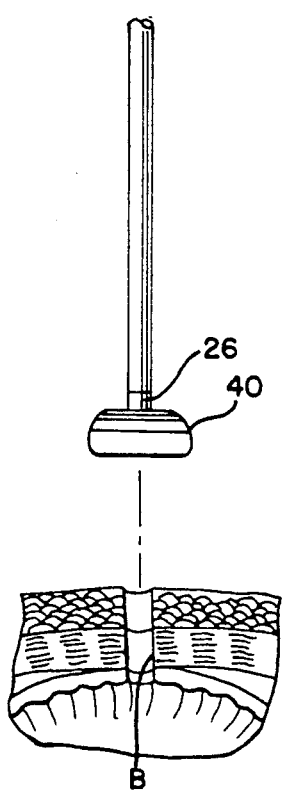

RETENTION BALLOON FOR PERCUTANEOUS CATHETER

DESCRIPTION

1. Technical Field

The present invention generally relates to catheters for placement within body vessels, cavities or organs such as in angioplasty, gastrostomy, cystostomy or jejunostomy tubes and, in particular, to an improved inflatable retention member for anchoring or retaining a catheter within a body cavity, organ or vessel.

2. Background of the Invention

The use of compressible and expandable retention members, such as balloons or cuffs, are well known in a wide variety of medical fields For example, U.S. Pat. Nos. 3,640,282 and 3,799,173 disclose expandable and compressible foam-filled retention cuffs used on endotracheal tubes. U.S. Pat. Nos. 4,795,430 and 4,900,306 also disclose the use of inflatable and compressible foam-filled retention balloons in percutaneous endoscopic gastrostomy tubes. Inflatable balloons carried on catheters also find clinical applications in angioplasty.

FIGS. 1 and 2 disclose a prior art inflatable retention member a in a fully inflated configuration. FIG. 1A discloses the same retention member in a fully deflated configuration. Preferably, retention member a is an annular shaped balloon secured near a distal open end b of a percutaneous catheter, such as a gastrostomy tube c having a fluid lumen d. Typically, balloon a is circumferentially secured solely to the outer wall of tube c.

Balloon a may be inflatable through an inflation lumen e and may also be pre-formed into the fully inflated outer configuration. Further, an inflation chamber f of balloon a may be substantially filled with a polyurethane foam g to urge balloon a to assume the inflated outer configuration. Foam g, however, is sufficiently compressible to permit balloon a to assume the deflated outer configuration shown in FIG. 1A.

One disadvantage of the structure of balloon a occurs upon deflation. As shown in FIG. 1A, because balloon a is circumferentially secured to the outer wall of tube b, upon deflation, the balloon collapses around the outer diameter of the tube. As a result, the overall outer dimensions of the deflated balloon exceeds the outer diameter of the tube. This causes extraction and removal of balloon a through the stoma more difficult and increases the risk of damage to the exit site of the stoma.

Another disadvantage of the structure of balloon a may be encountered if over-inflation of the balloon occurs, particularly where balloon a has a non-preformed inflated outer configuration. As a result of balloon a being adhered to the outer wall of tube b, the inflation chamber f surrounds the tube. In the event of over-inflation, the expansion pressure within inflation chamber f causes balloon a to compress the outer wall of the tube, thereby constricting fluid lumen d. As a result, fluid flow through fluid lumen d becomes impeded.

Hence, prior to the development of the present invention, a need existed for an inflatable and collapsible retention member for percutaneous tubes and other internally anchored catheters which would overcome these and other problems.

SUMMARY OF THE INVENTION

According to the present invention, an improved construction has been developed for an expandable and contractible retention member, such as a balloon, for percutaneous catheters and other catheters anchored or retained within a body cavity or organ. When deflated, the retention member of the present invention collapses upon itself rather than on the outer wall of the tube. This achieves an outer configuration no greater than the outer diameter of the tube itself. In addition, if over-inflated, the improved retention balloon of the present invention does not constrict fluid flow through the distal open end of the tube. Rather, the balloon of the present invention radially expands to increase an axial aperture passing through the balloon. This results in unimpaired fluid flow characteristics through a distal open end of the tube.

Generally, the inflation balloon of the present invention is an annular shape when fully inflated so as to retain a distal open end of the tube against an inner body cavity wall of the patient. This maintains the tube securely within the body cavity and prevents its inadvertent extraction through the surgically formed stoma. Unlike prior art retention balloons, the balloon of the present invention is secured to only the inner and outer peripheral edges of the distal open end of the tube. Specifically, the balloon of the present invention is adhered to both outer and inner walls of the peripheral edge of the distal end of the tube by means of a sleeve. The sleeve has both an outer wall and an inner wall which receives, respectively, the outer and inner walls of the tube.

The balloon includes an outer wall and an inner wall which defines inflation/retention chambers. Unlike prior art inflation balloons, the inflation/retention chambers extend beyond the distal open end of the tube so that no portion of the tube passes through the chamber. Instead, fluid flow through the fluid lumen of the tube passes through an axial opening in the balloon to permit passage of fluid out of the tube. Because of this construction, in the event of over-inflation of the balloon, the inflation/retention chambers radially expand so as to increase the inner dimensions of the axial opening with no constriction upon the fluid lumen of the tube.

Another beneficial result of the construction of the balloon of the present invention occurs upon deflation of the balloon. Again, because the inflation/retention chambers extend beyond the distal open end of the tube, upon deflation of the balloon the balloon collapses upon itself rather than around the outer wall of the tube. As a result, the outer dimensions or outer diameter of the deflated balloon approximates the outer diameter of the tube.

Other advantages and aspects of the invention will become apparent upon making reference to the specification, claims, and drawings to follow.

BRIEF DESCRIPTION OF DRAWINGS

FIG. 3 is a vertical section taken through one embodiment of the present invention shown in a fully inflated state;

FIG. 3A is the same view as FIG. 3 disclosing the balloon of the present invention in a fully deflated state;

FIGS. 4A–4C disclose the steps of extraction of a percutaneous tube having an inflation balloon of the present invention carried on a distal open end thereof;

DETAILED DESCRIPTION

Figure 2A:
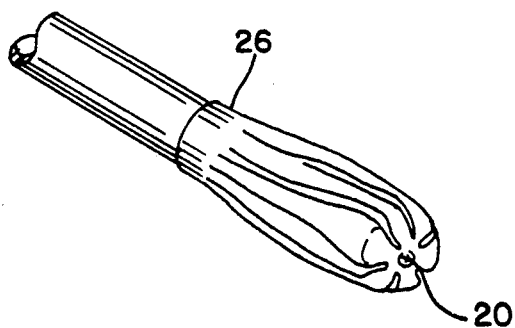
FIG. 2A is an inflation balloon of the present invention in a fully deflated state.

While this invention is susceptible of embodiment in many different forms, there is shown in the drawings and will herein be described in detail a preferred embodiment of the invention. The present disclosure is to be considered as an exemplification of the principles of the invention and is not intended to limit the broad aspect of the invention to embodiment illustrated.

Specifically, while the present invention is exemplified with reference to a percutaneous catheter, the present invention finds application for any catheter having an inflatable balloon for inflation within a body cavity, organ or vessel.

Referring now to the drawings, FIG. 3 generally discloses an inflatable retention member, preferably a balloon 10 made in accordance with the present invention. Balloon 10 preferably is made from a medical grade polyurethane plastic and is pre-formed into the fully inflated outer configuration disclosed in FIG. 3. By pre-forming balloon 10 into a fully inflated outer configuration, balloon 10 will repeatedly inflate to a uniform outer configuration. This assures that when balloon 10 is inflated within a body cavity of a patient, balloon 10 will assume a fully inflated state having an outer configuration of necessary size and proportion. However, it is possible for balloon 10 to have a non pre-formed outer configuration such that some variance will occur in the outer configuration of the balloon when it assumes a fully inflated state.

As disclosed in FIG. 3, balloon 10 is affixed to a distal open end 12 of a percutaneous access tube, such as a gastrostomy tube 14. Tube 14 has an outer wall 14A, an inner wall 14B and a fluid lumen 14C which accommodates fluid flow through the tube. Tube 14 must have a secondary inflation lumen 14D for inflation and deflation of balloon 10 in a manner to be described later.

Balloon 10 includes an outer wall 16 which is generally coextensive with outer wall 14A of tube 14. Outer wall 16 turns inwardly to define an inner wall 18. Inner wall 18 surrounds an axial opening 20 which is in fluid communication with fluid lumen 14C of tube 14. Hence, unlike prior art inflation balloons, fluid within tube 14 passes through balloon 10 itself.

Outer wall 1 and inner wall 18 of balloon 10 define an inflation/retention chamber 22 which may be substantially filled with a polyurethane, compressible foam 24. In this configuration, foam assists in the re-inflation of the balloon after insertion. The annular configuration of the balloon lends itself to re-inflation of the balloon without the presence of foam. The chamber may also be inflated manually via the use of a syringe containing fluid or air. Unlike prior art inflation balloons, inflation/retention chamber 22 of the present invention extends beyond the distal open end 12 of tube 14. This eliminates many of the disadvantages incurred upon inflation and deflation of balloon 10.

Balloon 10 is secured to the open distal end 12 of tube 14 by means of a sleeve 26 which preferably is integral with balloon 10. Sleeve 26 has an outer wall 26A and an inner wall 26B which are secured to outer wall 14A and inner wall 14B of tube 14 as shown in FIGS. 3 and 3A. Preferably, outer and inner wall sleeves 26 are RF welded in a manner to be described later in greater detail, or solvent bonded to outer wall 14A and inner wall 14B of tube 14 using techniques well know in the art.

As a result of the foregoing described structure, balloon 10, when in a fully inflated state, forms axial opening 20 which has inner dimensions generally the same as the inner dimensions of fluid lumen 14C. In the event that over-inflation of balloon 10, outer walls 16 radially expand outwardly in the direction of the arrows shown in FIG. 3. Rather than constricting axial opening 20 as in prior art inflation balloons, the axial opening 20 increases in inner dimension.

As best disclosed in FIGS. 2A and 3A, when in a fully deflated state, balloon 10 assumes an outer configuration no greater than the outer diameter of tube 14. Because inflation/retention chamber 22 extends beyond the open distal end 12 of tube 14, upon release of pressure within inflation/retention chamber 22, balloon 10 collapses upon itself during extraction through the stoma and the stoma exit site of the patient.

Figure 2B:
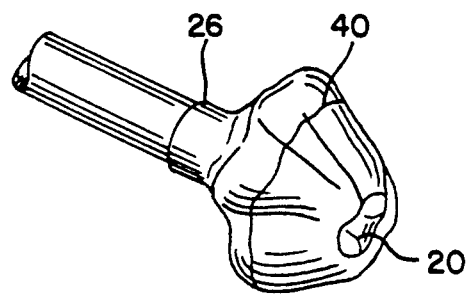
FIG. 2B is the same view as FIG. 2A disclosing the balloon of the present invention in an intermediate deflated state.
Figure 2C:
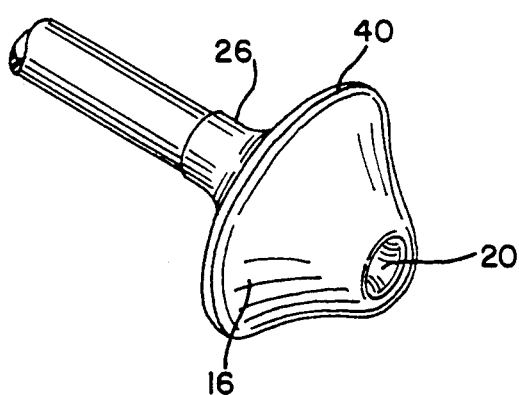
FIG. 2C is the same view as FIG. 2A disclosing the balloon of the present invention in an intermediate inflated state.
Figure 2D:
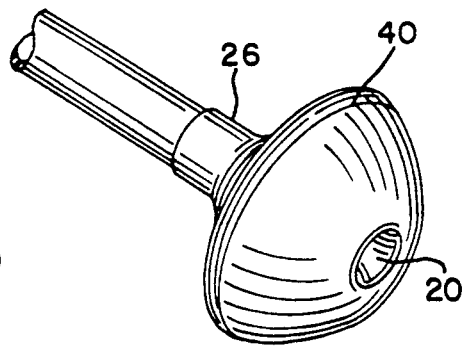
FIG. 2D is the balloon of the present invention disclosing a fully inflated state.
Figure 1:
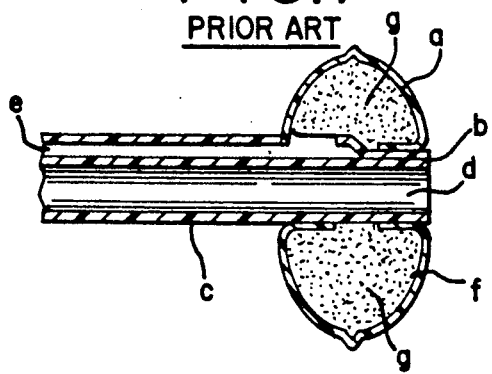
FIG. 1 is a vertical section taken through a prior art retention balloon in an inflated state.
Figure 1A:
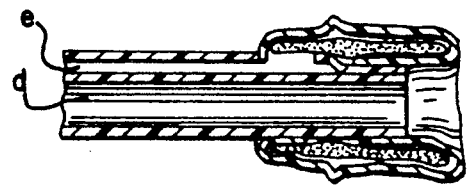
FIG. 1A is the same view as FIG. 1 disclosing the prior art balloon in a deflated state.

FIG. 2B discloses balloon 10 in a semi-deflated state in which axial opening 20 begins to form. In FIG. 2C, outer wall 16 of balloon 10 begins to assume the shape of the pre-formed fully inflated outer configuration which shape is completely assumed as disclosed in FIG. 2D.

FIGS. 4A, 4B and 4C disclose a method of extracting balloon 10 from within a body cavity and through the stoma and stoma exit site of a patient. FIG. 4A disclose balloon 10 having a fully inflated outer configuration and anchored within body cavity A. Due to the pliability of outer wall 16 of balloon 10, a health attendant can extract balloon 10 through stoma B. In so doing, the inner walls of stoma B urge balloon 10 into a deflated state as shown in FIG. 4B. Upon full extraction of balloon 10 as disclosed in FIG. 4C, balloon 10 reinflates due to the loss of pressure of inner walls of stoma B acting upon balloon 10.

Figure 5:
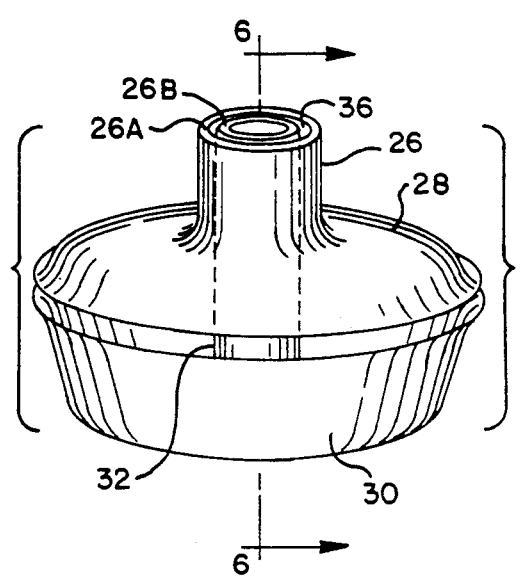
FIG. 5 is an exploded view of a preferred embodiment of the present invention.
Figure 6:
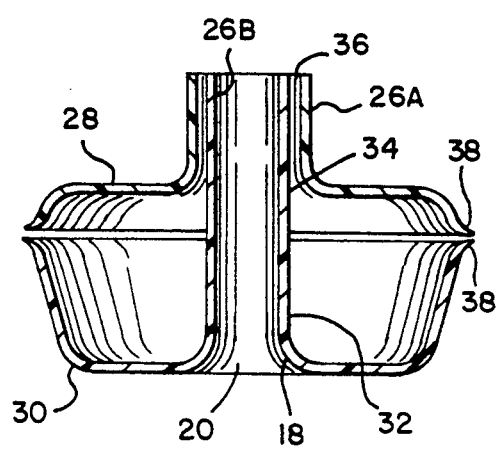
FIG. 6 is a vertical section taken along line 6—6 of FIG. 5.
Figure 7:
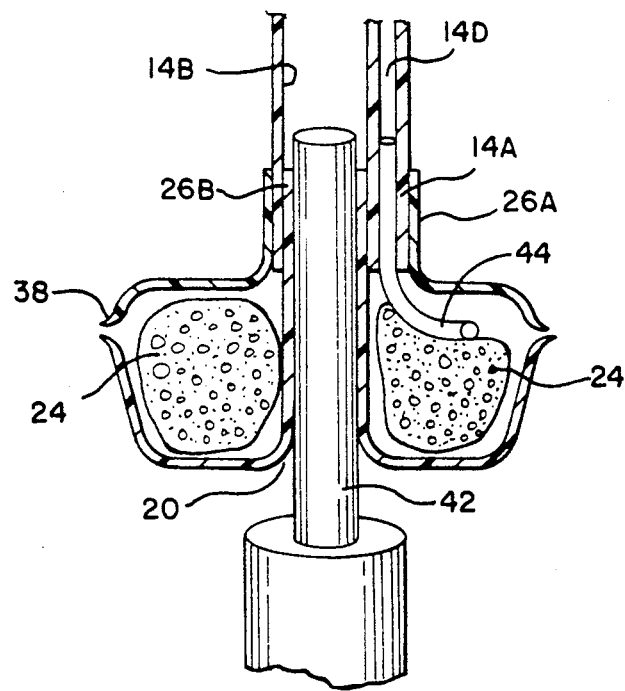
FIG. 7 discloses a preferred manufacturing method for the present invention.

FIGS. 5 through 7 disclose a preferred method of manufacturing balloon 10. As shown in FIGS. 5 and 6, balloon 10 is preferably formed from two molded elastomeric plastic parts, such as polyurethane or other elastomeric plastic parts. A proximal portion 28 defines a top half of balloon 10, and, a distal portion 30 defines a bottom half of balloon 10. Sleeve 26 preferably is integrally formed as part of proximal portion 28. This provides sleeve 26 with an outer core to function as outer wall 26A for securement to outer wall 14A of tube 14. Integrally formed in distal portion 30 is an inner core 32 of which an upper portion 34 functions as sleeve inner wall 26B for securement to inner wall 14B of tube 14. In upper portion 34, inner core 32 is inserted within sleeve outer wall 26A to complete the overall construction of sleeve 26. Defined between sleeve outer wall 26A and sleeve inner wall 26B is a circumferential gap 36 into which is inserted open distal end 12 of tube 14. Inner core 32 also defines axial opening 20 to receive fluid from fluid lumen 14C of tube 14. Two circumferential peripheral edges 38 on proximal portion 28 and distal portion 30 are slightly flanged. This permits the formation of a perimeter seal about the circumference of balloon 10 at the completion of the manufacturing operation.

FIG. 7 discloses a preferred method of RF sealing of sleeve 26 of balloon 10 to the distal end 12 of tube 14. First, proximal portion 28 is placed on tube 14 such that inner wall 26A contacts outer wall 14A approximately ⅛ inches from distal end 12 of tube 14. Then, inner core 32 of distal tube portion 30 is placed approximately ⅛ inches inside tube 14 through distal end 12. This permits inner wall 14B of tube 14 to contact sleeve inner wall 26B of core 32 of distal portion 30. Mandrel 44 is inserted into inflation lumen 14D of tube 14 and mandrel 42 is inserted into axial opening 20 until approximately 1/32 inches of mandrel 42 extends beyond the interface of the inner and outer walls of sleeve 26 in tube 14. Electronic welding, RF welding is then externally applied to seal and fuse sleeve outer wall 26A to tube outer wall 14A and sleeve inner wall 26B to tube inner wall 14B. During RF welding, mandrel 42 prevents fluid lumen 14C from closure while mandrel 44 prevents similar closure of inflation lumen 14D.

After RF welding has been completed, both mandrel 42 and 44 are removed. An annular or donut-shaped segment of foam 24 having a central hole is then placed within balloon 10. This is achieved by folding and deforming distal balloon portion 30 such that it can pass through the central hole in annual foam segment 24.

Finally, balloon 10 is completed by RF sealing together circumferential peripheral edges 38 on proximal portion 28 and distal portion 30, thereby forming a perimeter seal 40 about the circumference of balloon 10.

While the specific embodiments have been illustrated and described, numerous modifications come to mind without significantly departing from the spirit of the invention and the scope of protection is only limited by the scope of the accompanying claims.

We claim:

1. In a single body access tube having an inner surface and an outer surface defining a fluid lumen and an inflation lumen, the tube including an inflatable retention member carried near a distal open end of the tube, the member having an inflation/retention chamber surrounding the outer surface of the tube, the member circumferentially secured to the outer surface of the tube, the improvement comprising:

the member being circumferentially secured to the distal open end of the tube and to both the inner surface and the outer surface of the tube, the member having an axial opening communicating with the fluid lumen of the tube, the inflation chamber of the member being substantially foam filled and extending beyond the distal open end of the tube so that no portion of the tube passes through the chamber;

such that when inflated, the member projects beyond the distal end of the tube and assumes an outer configuration having an outer diameter greater than the outer diameter of the tube, when deflated, the member collapses upon itself and assumes an outer collapsed configuration having an outer diameter no greater than the outer diameter of the tube.

2. In a single body access tube having an inner surface and an outer surface defining a fluid lumen and an inflation lumen, the tube including an inflatable retention member carried near a distal open end of the tube, the member having an inflation/retention chamber surrounding the outer surface of the tube, the member circumferentially secured to the outer surface of the tube, the improvement comprising:

the member being circumferentially secured to the distal open end of the tube and to both the inner surface and the outer surface of the tube, the member having an axial opening communicating with the fluid lumen of the tube, the inflation chamber of the member being substantially foam filled wherein the foam includes a polyurethane foam, and further wherein the chamber extends beyond the distal open end of the tube so that no portion of the tube passes through the chamber;

such that when inflated, the member projects beyond the distal end of the tube and assumes an outer configuration having an outer diameter greater than the outer diameter of the tube, when deflated, the member collapses upon itself and assumes an outer collapsed configuration having an outer diameter no greater than the outer diameter of the tube.

3. A catheter having a single tube and adapted for retention within a body cavity, organ or vessel, comprising:

an inner surface and an outer surface defining a fluid lumen and an inflation lumen;

a distal end of the tube being open;

an inflatable retention member circumferentially secured to the open distal end and to both the inner surface and outer surface of the catheter, the member having an opening communicating with the fluid lumen of the catheter; and, the member having an inflation chamber extending beyond the distal open end of the catheter so that no portion of the catheter passes through the chamber and wherein the inflation chamber is substantially foam filled, such that the member, when inflated, projects beyond the distal end of the tube and assumes an outer configuration having an outer diameter greater than the outer diameter of the catheter, the member, when deflated, collapses upon itself and assumes an outer collapsed configuration having an outer diameter no greater than the outer diameter of the catheter.

4. A catheter having a single tube and adapted for retention within a body cavity, organ or vessel, comprising:

an inner surface and an outer surface defining a fluid lumen and an inflation lumen;

a distal end of the tube being open;

an inflatable retention member circumferentially secured to the open distal end and to both the inner surface and outer surface of the catheter, the member having an opening communicating with the fluid lumen of the catheter; and, the member having an inflation chamber extending beyond the distal open end of the catheter so that no portion of the catheter passes through the chamber and wherein the inflation chamber is substantially foam filled and the foam includes a polyurethane foam, such that the member, when inflated, projects beyond the distal end of the tube and assumes an outer configuration having an outer diameter greater than the outer diameter of the catheter, the member, when deflated, collapses upon itself and assumes an outer collapsed configuration having an outer diameter no greater than the outer diameter of the catheter.

5. A method of forming an inflatable retention member to be carried on a distal open end of a catheter, the catheter having a fluid lumen and an inflation lumen, the method comprising the steps of:

forming a proximal portion of the member, the proximal portion having a sleeve with a small diameter mating end to receive and contact an outer surface of the distal end of the catheter and the sleeve of the proximal portion having a large diameter mating end;

forming a distal portion of the member, the distal portion having a large diameter mating end for circumferentially mating with the large diameter mating end of the proximal portion, the distal portion having a core coaxial with the sleeve, the core being insertable within only the fluid lumen to contact an inner surface of the catheter;

bonding the sleeve to the outer surface of the catheter and the core to the inner surface of the catheter;

inserting between the proximal and distal portions a compressible material; and circumferentially bonding together the large diameter mating ends of the proximal portion and the distal portion.

* * * * *